United States Patent [19]

Fogarty et al.

[11] 4,292,974
[45] Oct. 6, 1981

[54] DILATATION CATHETER APPARATUS AND METHOD

[75] Inventors: Thomas J. Fogarty, 770 Welch Rd., Palo Alto, Calif. 94304; Albert K. Chin, San Francisco, Calif.

[73] Assignee: Thomas J. Fogarty, Palo Alto, Calif.

[21] Appl. No.: 116,816

[22] Filed: Jan. 30, 1980

[51] Int. Cl.³ .............................................. A61M 29/02
[52] U.S. Cl. .................................. 128/344; 128/349 B
[58] Field of Search ............ 128/344, 349 B, 349 BV, 128/303.11, 303.12, 341

[56] References Cited

U.S. PATENT DOCUMENTS

| | | |
|---|---|---|
| 2,616,429 | 11/1952 | Merenlender . |
| 2,688,329 | 9/1954 | Wallace . |
| 3,426,744 | 2/1969 | Ball . |
| 3,585,983 | 6/1971 | Kantrowitz ..................... 128/344 X |
| 3,692,018 | 9/1972 | Goetz ............................. 128/344 X |
| 3,799,172 | 3/1974 | Szpur . |
| 3,837,347 | 9/1974 | Tower ............................. 128/344 X |
| 4,046,151 | 9/1977 | Rose . |
| 4,105,022 | 8/1978 | Antoshkiw et al. . |

FOREIGN PATENT DOCUMENTS 512456  9/1939  United Kingdom ............ 128/349 B

*Primary Examiner*—Harland S. Skogquist
*Attorney, Agent, or Firm*—Naylor, Neal & Uilkema

[57] ABSTRACT

A dilatation catheter is provided with an inflatable section which in its non-inflated condition may have a diameter several times that of the balance of the catheter. Means are provided to axially twist the inflatable part of the catheter to reduce its diameter in its non-inflated condition to a size comparable to that of the non-inflatable balance of the catheter so that the catheter may be threaded through and positionally emplaced within a blood vessel.

8 Claims, 5 Drawing Figures

DILATATION CATHETER APPARATUS AND METHOD

BACKGROUND OF THE INVENTION

The present invention relates to a method and apparatus for use in dilating occluded blood vessels. The invention is particularly concerned with such a method and apparatus wherein dilatation is achieved through means of a balloon element of large diameter which is inflated to compress the occlusion being treated and wherein the transverse dimension of the non-inflated balloon element may be reduced to a minimal condition to enable placement of the catheter properly within the lumen of an occluded artery or vein.

SUMMARY OF THE INVENTION

In the dilation catheter of the present invention the catheter is provided with a ballonable wall portion which, both in its non-inflated and inflated conditions, has a diameter several times that of the balance of the catheter. This poses the problem as to how to pass the balloonable portion of the catheter conveniently and properly within the lumen of an occluded artery or vein. This problem is solved by axially twisting the balloonable portion so as to decrease its large non-inflated diameter to a reduced diameter of comparable size to that of the balance of the catheter for emplacement of the catheter. The balloonable portion is then untwisted in place to enable it to be blown up.

A principal object of the invention is to provide an inflatable dilatation catheter with a large diameter expansible portion and means to reduce the diameter thereof in the noninflated condition to a size which may be conveniently and efficiently moved into place within an occluded blood vessel.

Another object of the invention is to provide such a catheter with fluid sealing means which is in sealed condition when the diameter of the non-inflated inflatable portion is large and which is in unsealed condition when the diameter of the noninflated inflatable portion is small.

These and other objects and advantages of the invention will be apparent from the description taken in conjunction with the drawing forming part of this specification.

DESCRIPTION OF THE PREFERRED EMBODIMENT

Figure 1:
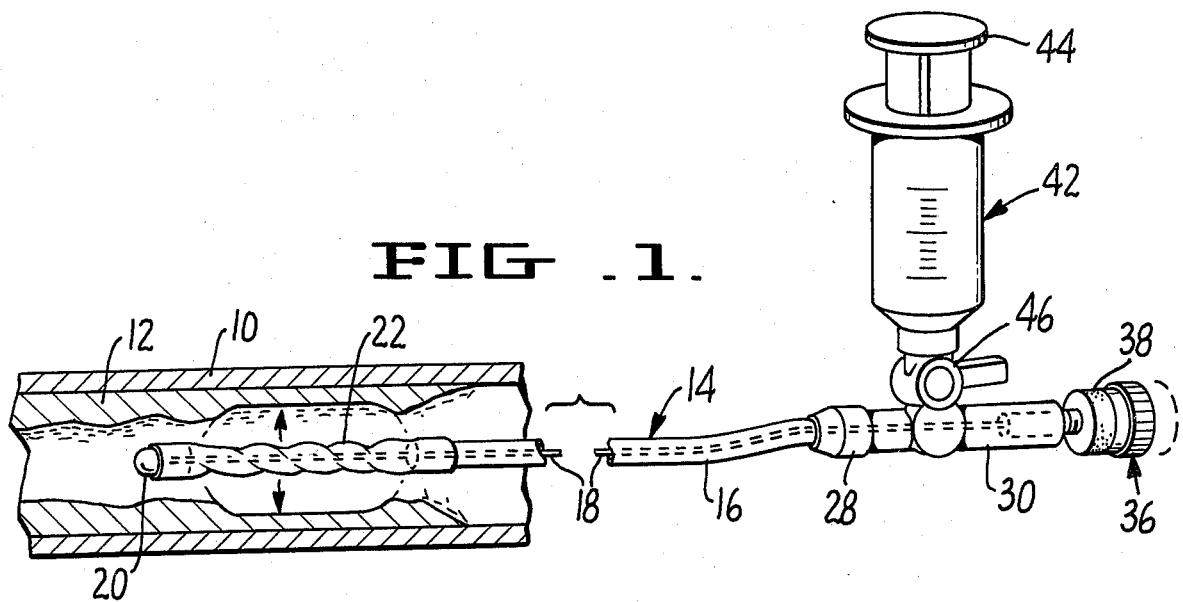
FIG. 1 is a view partly in perspective and partly in section of the subject catheter and an occluded artery.

FIG. 1 illustrates a blood vessel 10 which is partially occluded by an extended occlusion 12. As shown, the vessel takes the form of an artery and the occlusion is what is commonly known as an arteriosclerotic plaque or atheroma. This is the type of adhering occlusion with which the subject apparatus and method is expected to find primary application. It should be understood, however, that the inventions are applicable in treating other types of occluded vessels where dilatation is desired. For example, the inventions may be used in treating occlusions resulting from fibromuscular displasia in veins.

The catheter 14 comprises a flexible plastic tube 16, a guide wire 18 extending therethrough and fixedly attached to rounded tip member 20, an inflatable bag 22 having its ends 24 and 26 bonded to tube 16 and tip member 20. Tube 16 is fixedly attached to an internally threaded coupling member 28 which is attached to the externally threaded end of a T-shaped fitting 30. The proximal end of fitting 30 is provided with internal threads 32 with which the externally threaded stem portion 34 of control knob 36 is threadably engageable. Control knob 36 is fixedly attached to wire 18. The knob stem 34 is normally fully threadably engaged with fitting 30 to thereby position the sealing disc 38 carried by knob 36 in sealing engagement with the proximal end 40 of fitting 30.

A syringe 42 is connected to the proximal end of the catheter 14 through the fitting 30. The syringe is to be filled with an incompressible fluid, and a plunger 44 forming part of the syringe and a control valve 46 constitute means whereby this fluid may be selectively charged into or released from the dilatation bag or balloon 22 through the tube 16.

Figure 2:
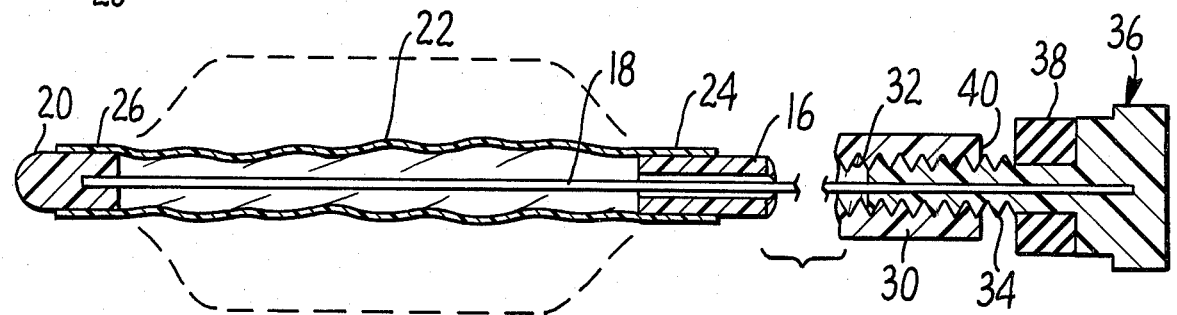
FIG. 2 is an enlarged view in section of the subject catheter.

The catheter is used in the following manner. The knob 36 is rotated to back it off from the fitting 30 to approximately the position shown in FIGS. 1 and 2. The wire 18 and tip 20 are thereby rotated to wind up or twist the bag 22 to thereby materially reduce the non-inflated diameter of the bag to a value of that of tube 16 or less. As the wire and tip are rotated to twist the bag the tip 20 moves closer to the distal end of tube 16 and the bag 22 becomes shortened in corresponding relation to the degree of twist imparted thereto. The more and tighter the balloon is twisted, the lesser becomes its diameter and the greater is the stiffness imparted to the balloonable section of the catheter by the twisted condition of the balloon. The twisted condition of the balloon, due to the greatly reduced non-inflated diameter thereof and to the proportionately increased stiffness thereof, contributes substantially to the efficient feeding of the catheter along the blood vessel and to its desired emplacement relative to atheroma 12. As usual the catheter is introduced into vessel 10 through an incision, not shown.

Figure 3:
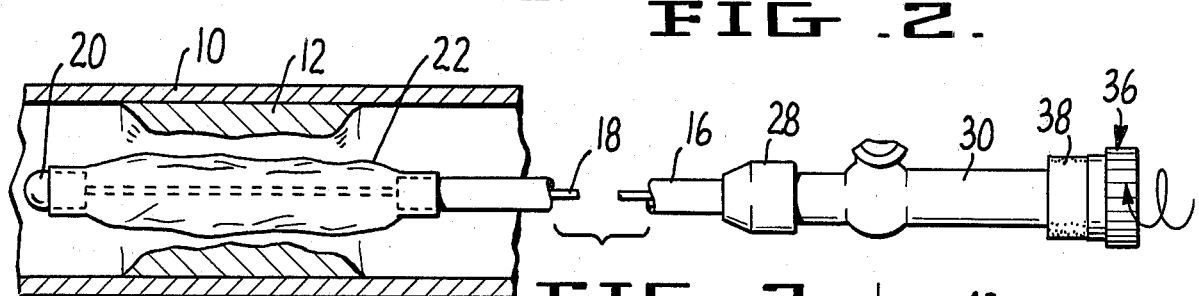
FIG. 3 is a view partly in elevation and partly in section showing the subject catheter emplaced in an occluded artery and ready for inflation of the dilatation element.
Figure 4:
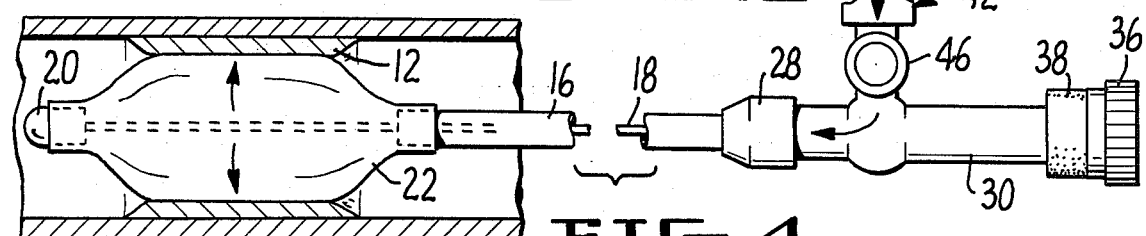
FIG. 4 is a view similar to that of FIG. 3 but showing the dilatation element in inflated condition.
Figure 5:
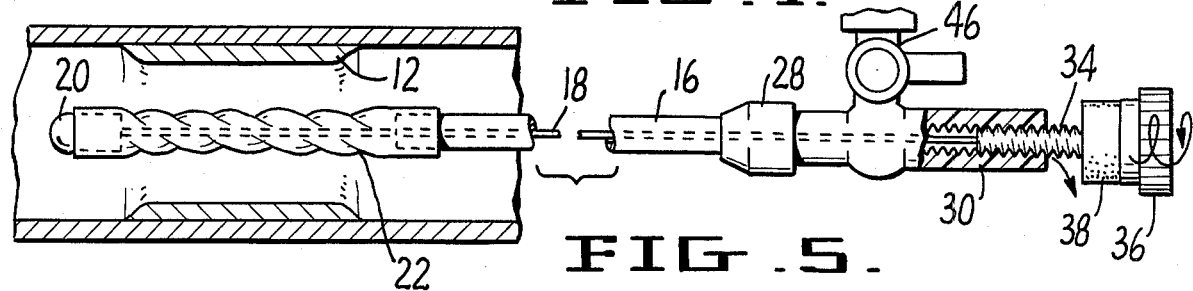
FIG. 5 is a similar view showing the catheter in condition for removal from the artery.

When the catheter has been properly emplaced relative to the atheroma 12, as shown in FIG. 3, the knob 36 is turned in the opposite direction to bring the sealing disc 38 into abutting and sealing relation with the end 40 of fitting 30. Consequent rotation of wire 18 and tip 20 results in the untwisting and resultant lengthening of bag 22. The untwisted condition of the bag is shown in FIG. 3. Valve 46 and plunger 44 are then operated to inflate bag 22 with incompressible fluid and cause it to press against and compact the atheroma 12. Valve 46 is closed to maintain the inflated condition of bag 22 for a suitable period of time. After the atheroma has been effectively compressed by the bag, the control knob 36 is once again backed off from the fitting 30, as illustrated in FIG. 5, to move the sealing disc 38 away from the fitting and wind up or twist the bag 22. The twisting of the bag and consequent reduction of its diameter forces the fluid out of the bag and causes it to drain out of the catheter through the now unsealed end 40 of fitting 30. The catheter may then be moved to a new section of atheroma to be treated or be withdrawn from the vessel, as the case may be.

The catheter may be provided with a quick-connect connection between knob 36 and fitting 30 such that in a turn or less of the knob the latter is either fully connected or fully disconnected relative to fitting 30. In such an embodiment substantially all of the twisting and untwisting of the balloon element takes place while the knob is fully disconnected from fitting 30.

Conclusion

The apparatus and method of the present invention are ideally suited for the dilatation of elongate arterial occlusions by progressive and incremental dilatation, and in particular where it is important that the inflated diameter of the balloon element be several times the diameter of the catheter tube. Due to the mechanical contraction technique employed, the balloon element (bag 22) may provide for such inflation while being of a highly flexible thin-walled generally inelastic construction. It is to be understood, however, that this invention is not intended to be limited to the specific details described above but is rather to be defined by the terms of the appendant claims.

What is claimed is:

1. A dilatation catheter comprising an elongated flexible tubular body member, a tip member in spaced relation to the distal end of said body member, an annular inflatable bag interconnecting said tip member and said distal end of said body member, a wire extending through said body member and said bag and secured to said tip member, and knob means attached to the proximal end of said wire enabling said wire to be rotated about its longitudinal axis to rotate said tip member and axially twist said bag and thereby decrease the diameter of said bag in its noninflated condition.

2. The catheter of claim 1, said bag having a diameter in its non-inflated untwisted condition which is substantially greater than the diameters of said tip member and said body member.

3. The catheter of claim 1, further comprising a tubular fitting, said body member being attached to the distal end thereof and said knob means being attached to the proximal end thereof, and means connected to said fitting to impart an internal fluid pressure condition to said bag through said body member to selectively inflate said bag.

4. The catheter of claim 3, said knob means comprising an end portion variably threadably engageable with said fitting such that when it is threadably engaged therewith to a predetermined degree said bag is in an untwisted condition for inflation.

5. The catheter of claim 4, said knob means including sealing means operable when the end portion of said knob means is threadably engaged with said fitting to said predetermined degree to prevent the flow of fluid from the proximal end of said fitting, the thread engagement between said end portion of said knob means and said fitting providing for fluid passage therepast when said end portion and said fitting are threadably engaged to an extent less than said predetermined degree.

6. The catheter of claim 5, said sealing means being disposed in sealing engagement with the proximal end of said fitting when said end portion and fitting are threadably engaged to said predetermined degree and being disposed out of sealing engagement therewith when they are threadably engaged to an extent less than said predetermined degree.

7. A method for inserting an inflatable balloon into a partially occluded section of a blood vessel comprising axially twisting the balloon to reduce its diameter for passage along said vessel and into said partially occluded section, moving said balloon along said vessel while maintaining its axially twisted condition to emplace it in said section, axially untwisting said balloon while it is in place within said section, and inflating said balloon in place within said section.

8. The method of claim 7, including removing said balloon from said vessel comprising deflating said balloon while it is in place within said section, axially twisting the balloon while it is in place within said section to reduce its diameter for passage along said vessel, and moving said balloon along said vessel and out of said vessel.

* * * * *